United States Patent
Chen et al.

(10) Patent No.: US 7,410,493 B1
(45) Date of Patent: Aug. 12, 2008

(54) METHOD AND DEVICE FOR THE TREATMENT OF ANXIETY DISORDERS

(76) Inventors: Yu Chen, 1520 Taylor Ave., Baltimore, MD (US) 21234; Ming An Chen, 1520 Taylor Ave., Baltimore, MD (US) 21234

( * ) Notice: Subject to any disclaimer, the term of this patent is extended or adjusted under 35 U.S.C. 154(b) by 1134 days.

(21) Appl. No.: 09/570,909

(22) Filed: May 15, 2000

(51) Int. Cl.
*A61B 17/00* (2006.01)

(52) U.S. Cl. .................................. 606/204

(58) Field of Classification Search .......... 601/107; 606/204, 189; 128/898
See application file for complete search history.

(56) References Cited

U.S. PATENT DOCUMENTS

| | | | | |
|---|---|---|---|---|
| 2,970,592 | A * | 2/1961 | David | 606/238 |
| 4,669,454 | A * | 6/1987 | Shamos | |
| 4,745,910 | A * | 5/1988 | Day et al. | 601/41 |
| 5,484,386 | A * | 1/1996 | Masaki | 601/21 |
| 5,662,686 | A * | 9/1997 | Newsum | 606/238 |
| 5,676,684 | A * | 10/1997 | Choi | 606/189 |
| 5,766,210 | A * | 6/1998 | Komoroczy et al. | 601/135 |
| 5,836,901 | A * | 11/1998 | Shenkal et al. | 601/135 |
| 5,950,635 | A * | 9/1999 | Garcia-Rill et al. | 128/898 |
| 6,074,410 | A * | 6/2000 | Kim | 607/88 |
| 6,228,042 | B1 * | 5/2001 | Dungan | 601/107 |
| 6,361,550 | B2 * | 3/2002 | Grey et al. | 606/204 |
| 6,551,261 | B1 * | 4/2003 | Jun | 601/107 |

OTHER PUBLICATIONS

Chinese Acupuncture and Mosibustion, Cheng Xinnong, Foreign Lanuages Press Beijing, pp. 177-183, dated 1999.
Human Physiology, Robert F. Schmidt and Gerhard Thews Sprinher, "The Autonomic Nervous System", Verlag, Berlin, Heidelberg, New York, pp. 111-123, 126, 127, 140, 141, 193-197, dated 1983.
Comprehensive Textbook of Psychiatry/VI, Sixth Edition, Harold I. Kaplan and Benjamin Sadock, Williams & Wilkins, Chaper 17, pp. 1191-1195, 1198-2001, 1204, 1205, 1208-1249, dated 1995.
R. Reid Wilson, Ph.D., "Don't Panic—Taking Control of Anxiety Attacks", Harper perennial, pp. 3-41, dated 1987.
Deepak Chopra, M.D., "Alternative Medicine", Future Medicine Publishing, Inc., pp. 37-38, dated 1994.
The Pain Relief Breakthrough—The Power of Magnets, Julian Whitaker, M.D. and Brenda Adderly, M.H.A., Little, Brown and Company, dated 1998.

* cited by examiner

*Primary Examiner*—Todd E. Manahan
*Assistant Examiner*—Ryan Severson
(74) *Attorney, Agent, or Firm*—Sam Silverberg (57) ABSTRACT

A method and device for the treatment of anxiety disorder, including panic attacks. A hammer is used to tap the cutaneous region of the bladder channel on the back until the skin turns pink. The skin on the abdomen, arms, legs, and buttocks can also be used for treatment. The hammer preferably has a magnetic piece in one end of the hammer head. The method can treat anxiety disorder including panic attack, general anxiety, phobia, posttraumatic stress disorder, stress related tension headache, insomnia, and any stress. Patients can use the hammer to treat themselves at home, office, and during traveling. The method and device are simple, effective, non-toxic, safe, have no side effects, inexpensive, and convenient.

18 Claims, 7 Drawing Sheets

METHOD AND DEVICE FOR THE TREATMENT OF ANXIETY DISORDERS

BACKGROUND OF THE INVENTION

1. Field of the Invention

The present invention pertains to a method and a device for the treatment of anxiety disorders including panic attacks.

2. Description of Related Prior Art

Anxiety disorders are common psychiatric illnesses associated with considerable morbidity and social cost. Panic attack is one form of anxiety disorders. The criteria for panic attack diagnosis is in DSM-IV (Diagnostic and Statistical Manual of Mental Disorders ed. 4). One published epidemiological study using DSM-III-R panic disorder criteria found a lifetime prevalence of 3.5 percent. Of course many sufferers are undiagnosed, misdiagnosed, or untreated. Patients with panic attack suffer severely by the sudden onset of fear of dying, fear of insanity, palpitations, shortness of breath, chest pain, sweating, choking, and dizziness.

In Western medicine, there have been three main approaches to the treatment of anxiety disorders—pharmacotherapy (medications), non-medication therapies such as cognitive-behavioral therapy (discussion, relaxation, other psychological methods) and combinations of the two approaches. All three approaches have been helpful to some degree in many patients but have not been entirely satisfactory.

For pharmacotherapy treatment, it is important that the patient be aware of drug side effects and possible interactions with other medications. Effective types of medication include tricyclic antidepressants, monoamine oxidase inhibitors, benzodiazepines, and serotonergic agents.

Imipramine, a tricyclic antidepressant, has been shown to be helpful in double blind studies. The acute effect of imipramine is to block the re-uptake of the neurotransmitters, norepinephrine and serotonin, from the synaptic cleft into the presynaptic neuron. Many patients are sensitive to impipramine (side effects), but high doses are necessary to be helpful. Other tricyclics, such as desipramine (Norpramine), amitryptaline (Elavil), doxapin (Adapin), nortryptaline (Pamdor), and chloripramine (Anatranil) may also be effective dicyclics, but not well tolerated by all patients and are dangerous if overdosed.

Monoamine oxidase inhibitors, for example phenelzine (Nordil), are also somewhat effective antipanic agents by inhibiting the extraneuronal enzyme, monoamine oxidase, from metabolizing monoamines. Three to six weeks of drug administration are necessary before the drug becomes effective. The main drawback is the tendency of these drugs to develop the tyramine effect, allowing tyramine to enter the blood and provoke a hypertensive crisis.

Special diazepams, such as alprozalam (Xanax) and clorazepam (Klonopin), are somewhat effective against panic attack. It is believed that these drugs attach to benzodiazepine receptors in the brain, thus inhibiting neurons by inhibiting chloride ionophores. Conventional diazepams such as Valium are not reliable for blocking panic attacks.

Still another class of antipanic medications is seratonin-specific reuptake inhibitors (SSRIs) such as paroxetine (PAXIL) and sertaline (ZOLOFT). This group of drugs is characterized by its ability to selectively inhibit the reuptake of seratonin. Although SSRIs are effective in open trials, controlled studies have not yet been published. SSRIs can also cause gastrointestinal distress, hypomania, headaches, sexual dysfunction, and insomnia.

Non-medication approaches include (1) cognitive therapy and psycho educations, (2) applied relaxation, (3) respiratory control, and (4) exposure therapy. Cognitive therapy techniques include convincing the patient that the panic attack is short-lived and not very serious. Applied relaxation includes progressive muscle relaxation and thought control. Respiratory control techniques are to prevent hyperventilation. Exposure therapy means confrontation of the patient with the panic stimulus. Sometimes the combination of pharmacotherapy and cognitive therapy provides effective results.

All the above treatments have some merit, but they tend to have a slow and incomplete effect. In addition, the treatments can be expensive and the medications can be somewhat toxic. It is desirable to have a simple, effective, nontoxic, safe, inexpensive, time-saving, and convenient treatment for panic disorders.

SUMMARY OF THE INVENTION

The invention is directed to a method for the treatment of anxiety disorders including panic attacks. In the treatment of the invention, a hammer is used to tap the skin on the back, legs, arms, abdomen, or buttocks until the skin appears pink. The hammer stimulates the cutaneous regions of the acupuncture meridian channels and adjusts the body and mind to a relaxed level. Preferably, the hammer is used to tap the skin on bladder channel back shu points region until the skin becomes pink.

The treatment method of the invention provides an immediate and long lasting relaxing effect. This treatment can also reduce the frequency, intensity, and duration of panic attacks. In addition, there are no side effects or toxicity problems such as found with pharmacotherapy. The treatment of the invention is also beneficial for panic attack with phobias and other types of anxiety disorder such as general anxiety, posttraumatic stress disorder, obsessive compulsive disorder, stress related insomnia, tension headache, and common stress.

The invention is further directed to using a magnetic hammer with the method for the treatment of anxiety disorders. In one embodiment, the hammer has a magnetic head with a magnetic strength of from about 100-14000 gauss, preferably 800-2000 gauss.

The method of the invention can be practiced by health practitioners as well as by family members, friends, or even the patients themselves, at home, office, and during traveling. In addition, the hammer and the instructions are inexpensive.

BRIEF DESCRIPTION OF THE DRAWINGS

FIGS. 1a and 1b together show the relationship of back shu points and the sympathetic nerve ganglia. FIG. 1a shows the back shu points.

DETAILED DESCRIPTION OF THE INVENTION

Most symptoms of anxiety disorders, in particular panic attacks, are the result of sudden and excessive excitation of the sympathetic nervous system. The invention is directed to a treatment aimed at calming down the excited sympathetic nervous system by tapping with a hammer the cutaneous regions of acupuncture meridian channels.

In Chinese acupuncture, meridian channels and acupoints are used to adjust the function of the body in order to achieve balance. On bladder channels there are many acupoints on the back which are called "back shu points" FIG. 1a. The back shu points share the same horizontal and vertical locations with sympathetic nerve ganglia FIG. 1b. Although not wishing to be bound by any theory, it is believed that the back shu points are the skin representatives of the sympathetic nerve ganglia. Treating the back shu points area can calm down the sympathetic nervous system and adjust the body and mind to a relaxed level. Historically, acupuncture needles were used to treat the back shu points areas. The invention is directed to using a hammer instead of acupuncture needles to stimulate the skin in order to get an effect similar to acupuncture. A small hammer is used for tapping the selected skin area of the meridian channels. Tapping with the hammer stimulates the cutaneous regions of the acupuncture meridian channels, adjusting the body and mind to get to a relaxed level.

Although the mechanism of acupuncture is unknown, many studies show that electrical resistance is lower in the meridian channels and at acupoints than in areas adjacent to these points. Electrical energy is closely related to magnet energy and there are both electrical and magnetic energy fields in the body. Thus, a preferred embodiment of the invention takes advantage of the relationship between electrical and magnetic energies by using a hammer having a magnetic head to treat a patient. A small hammer with a magnetic head is thus used for tapping the selected skin area of the meridian channels.

Figure 2:
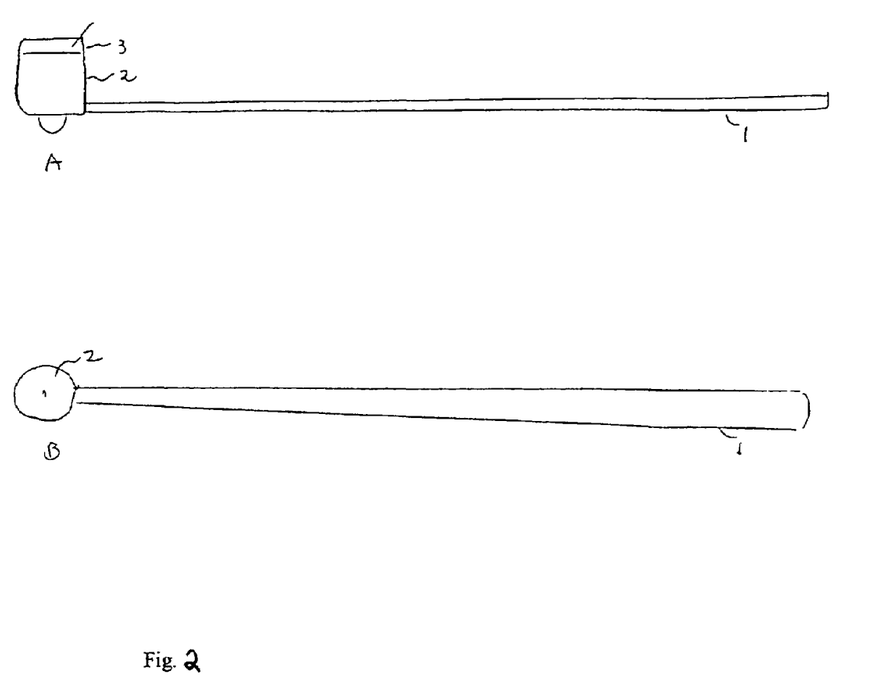
FIG. 2 is a drawing of a hammer having a magnetic head.

FIG. 2 is a drawing of the hammer. A is the side view of the hammer. B is the top view of the hammer. The hammer has a handle (1), which is preferably about 11-20 cm long. The hammer also has a head (2), which is preferably of a cylindrical shape with a diameter of about 10-15 mm. Other hammer head shapes include, but are not limited to, cubic, rectangular, or oval. A magnetic piece (3) is placed at the top side of the hammer head (opposite the handle side) and preferably cover just the top side of the hammer head. The magnetic strength of the piece is about 100-14,000 gauss, preferably about 800-2000 gauss.

Although a magnetic hammer is preferred, a non-magnetic hammer may be used in the method of the invention. The non-magnetic hammer may be a rubber head hammer, wooden head hammer, plastic head hammer, or any other suitable hammer.

Figure 3:
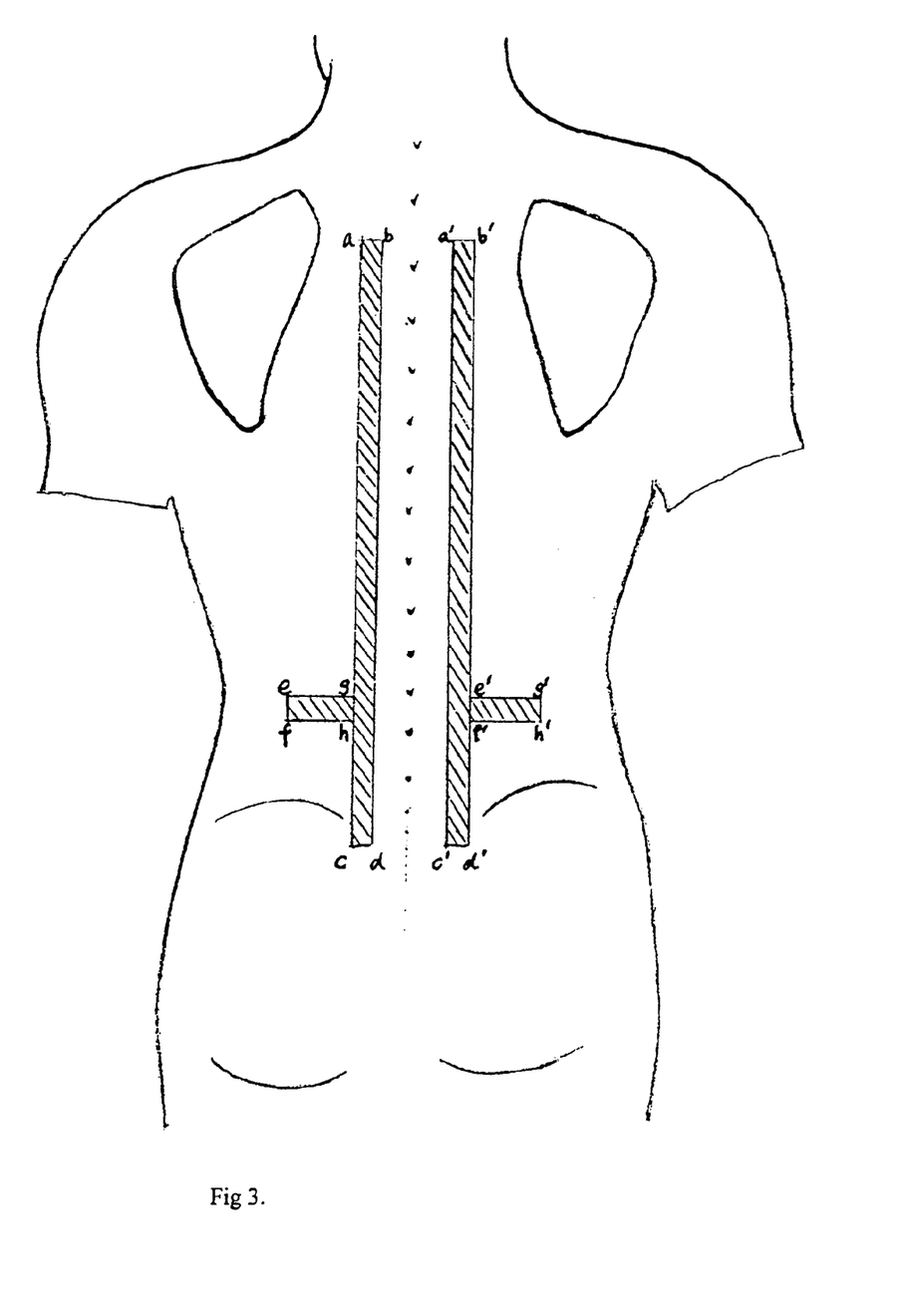
FIG. 3 shows the locutions on the back for tapping.

The hammer is used to hammer certain areas of the body. FIG. 3 shows the locations on the back for tapping. The shadow parts are the skin area for tapping. The top level area is represented by ab and a'b' and the bottom level area is represented by cd and c'd'. The top level ab and a'b' are at about the thoracic vertebral 3 level. The bottom level cd and c'd' are at about the lumbar vertebral 4 or sacroiliac 1-2 level. The areas represented by bd and a'c' are about 1.5 inches away from the spine. The areas represented by ef and e'f' are the horizontal tapping level, which are at about the lumbar vertebral 2 level. The width (ab, a'b' or cd, c'd') of the tapping area is about 1 inch. At the lumber 2 area the tapping length is 1 inch (ef, e'f') and the width is 3 inches on each side (eg, e'g'). Preferably, one should tap from top to bottom on both left and right sides until the skin gets pink. Then tap the horizontal areas until the skin appears pink.

The tapping area is the back on both sides of the spine, about 1 to about 2 inches, preferably about 1.5 inches) away from the spine between the thoracic vertebral 3 and the sacroiliac vertebral 4 level wherein the width of the tapping area is about 1 to about 1.5 inches on both sides of the spine. The tapping area is at about lumbar 2 vertrbral level, the width of the tapping is about 3 to about 4 inches on both sides of the spine.

Figure 4:
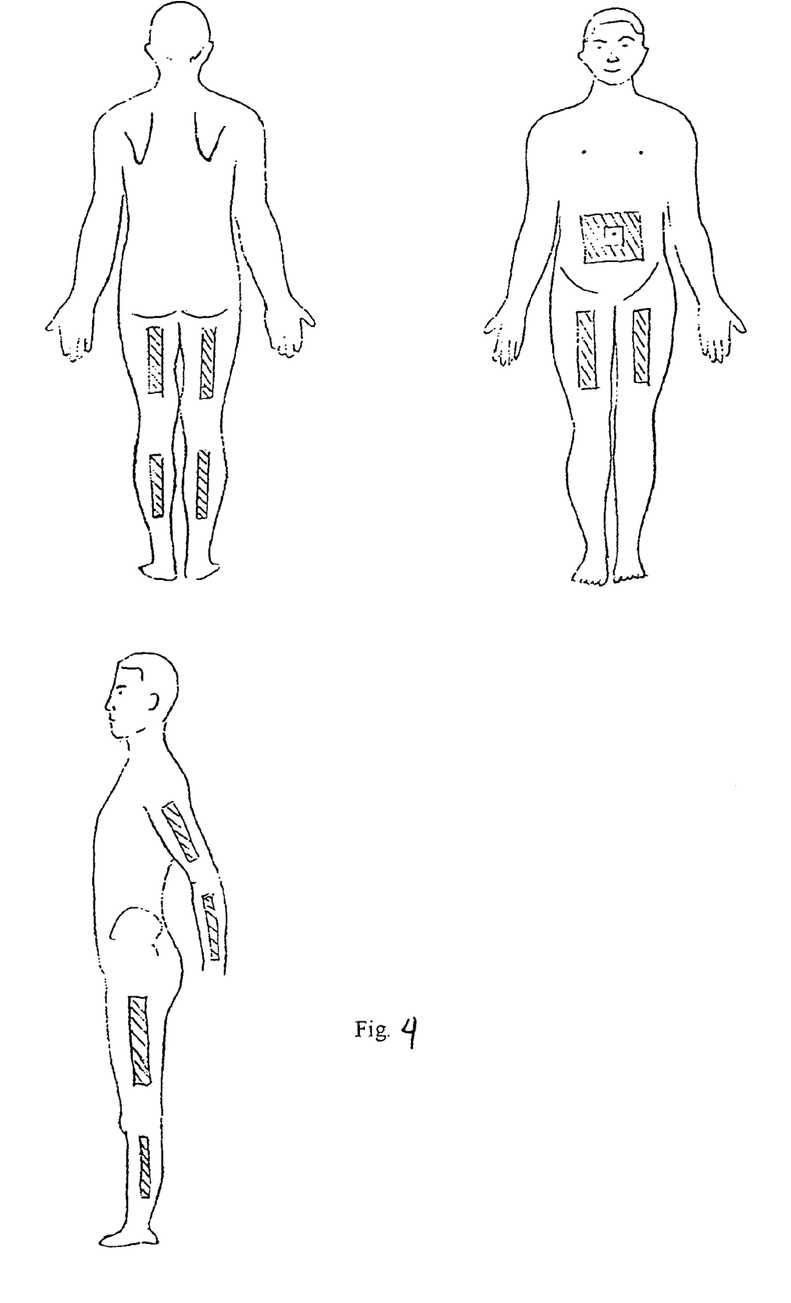
FIG. 4 indicates the areas on abdomen, legs, and arms for tapping.

FIG. 4 indicates the areas on abdomen, legs, and arms for tapping. On the abdomen, the area for tapping is about 0.5 inch to about 1 inch away from the navel and then about 2 to about 3 inches in each direction. On the arms, the tapping area is preferably the outer side of the upper arm or the outer side of the forearms. On the legs, the tapping area is preferably on the front, side, or back of the upper legs, or the back or side of the lower legs. In these area the tapping techniques is the same as with tapping the back.

Figure 5:
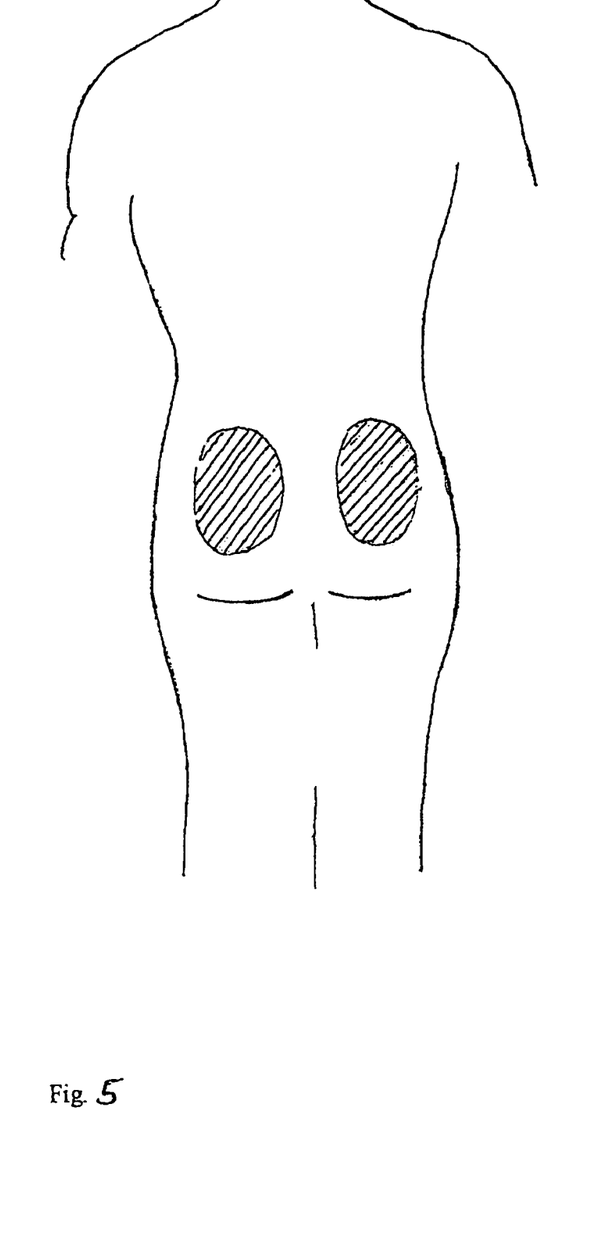
FIG. 5 indicates the areas on the buttocks for tapping.

FIG. 5 indicates the areas on the buttocks for tapping. The areas include both the right and left buttock areas.

The frequency of the treatment depends on the patient' emotional situation and the environment. If a patient has several episodes of panic attacks every day, once a day treatment may be necessary. Otherwise treatment is typically once a week or twice a week or when needed. When it is known that a life-stressful event will occur, the treatment may be administered prior to the event, preferably prior to any panicky or jittery feeling. The treatment may be stopped after the patient is relaxed and not experiencing any panic attacks, but should be resumed if a stressful feeling returns. Generally, the number of treatments can vary from a single treatment to several treatments over a period of the time such as from one month to three months. The duration of the treatment is not dependent on the location of the tapping and generally is about 5-10 minutes depending on the speed of the tapping. The skin of the selected area should become pink. If the color of the skin does not change or does not pink up, more tapping is necessary. If the skin turns red, the tapping has continued too long or is too strong. Strong tapping is not recommended. The pressure of each tapping is generally about 17-28 gram/cm$^2$.

Anxiety disorders are common and chronic diseases. Panic attacks, in particular, have intolerable episodes. Panic attack shows numerous symptoms of sympathetic nervous system and adrenal gland excitation. The symptoms of panic attacks include accelerated heart rate, sweating, trembling or shaking, sensations of shortness of breath or smothering; feeling of choking, chest pain or discomfort, nausea or abdominal distress; feeling dizzy, unsteady, light-handedness, or faintness, derealization, or depersonalization; fear of losing control or going crazy, fear of dying, paresthesia, chills, or hot flushes. (Diagnostic and Statistical Manual of Mental Disorders ed 4).

The autonomic nervous system controls the activity of the internal organs of the body. The autonomic nervous system is composed of the sympathetic nervous system and the parasympathetic nervous system. The transmitter substances in the sympathetic nervous system are epinephrine and norepinephrine, which come from the adrenal medulla. The transmitter substance in the parasympathetic nervous system is acetyl choline(Ach).

The sympathetic nervous system, including the adrenal medulla, through its integration relating to emotional behavior, prepares the body for somatic and visceral requirements. Most of these symptoms of panic attack can be explained by sympathetic nervous system excitation. If the sympathetic nervous system can be calmed, the symptoms of the panic attacks should be reduced or cease.

In the sympathetic system, the cell bodies of the preganglionic sympathetic neurons are in the lateral horn of the thoracic and lumbar spinal cord. The axons of these neurons terminate in the paired paravertebral ganglia or the unpaired prevertebral ganglia. In the ganglia there are neurons (nerve cells) which have postganglia axons. The sympathetic nerve ganglia are located on both sides of the spine. The paravertebral ganglia are connected by nerve strands to form a chain on either side of the vertebral column, extending from the base of the brain to the sacrum. From these sympathetic trunks the postganglinonic axons either extend into the effectors in the periphery of the body, or form special nerves that supply organs in the head, thorax, abdomen, and pelvis regions.

Figure 1A:
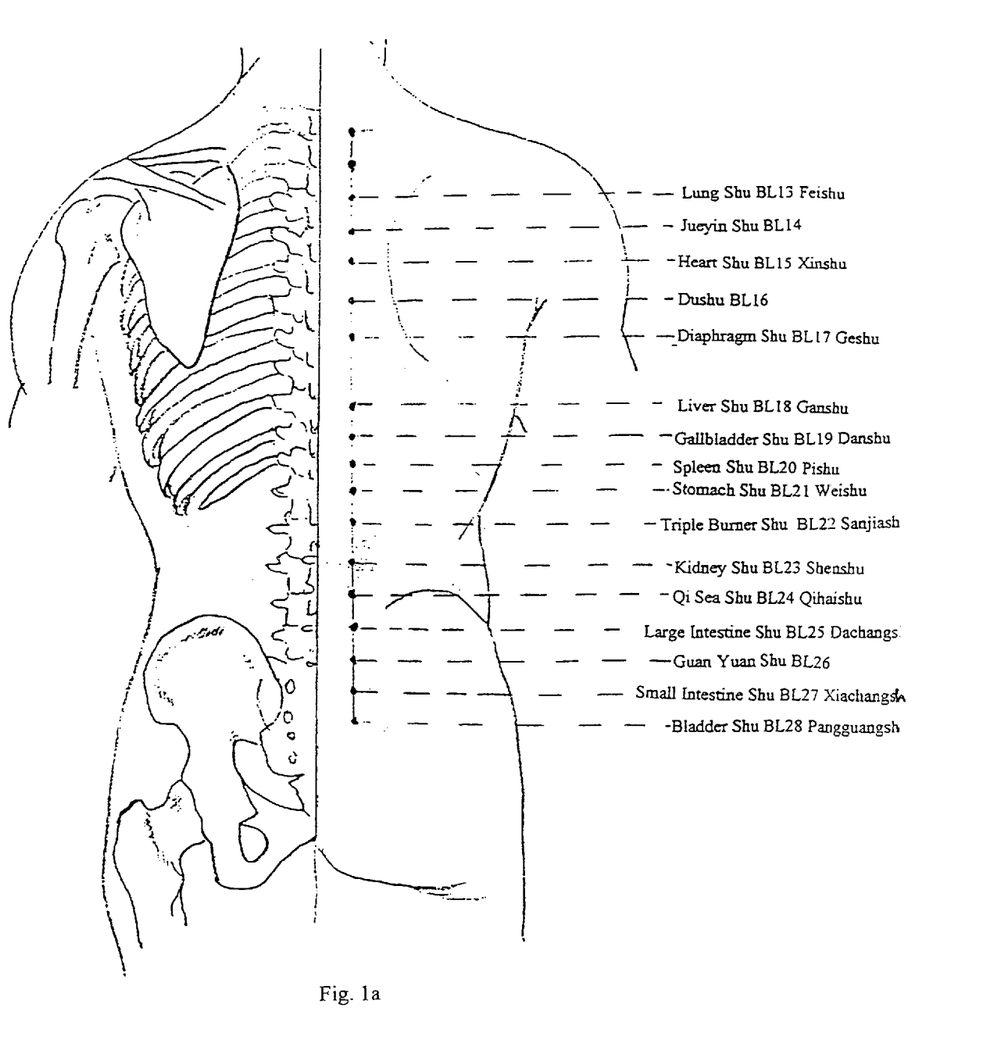
Figure 1B:
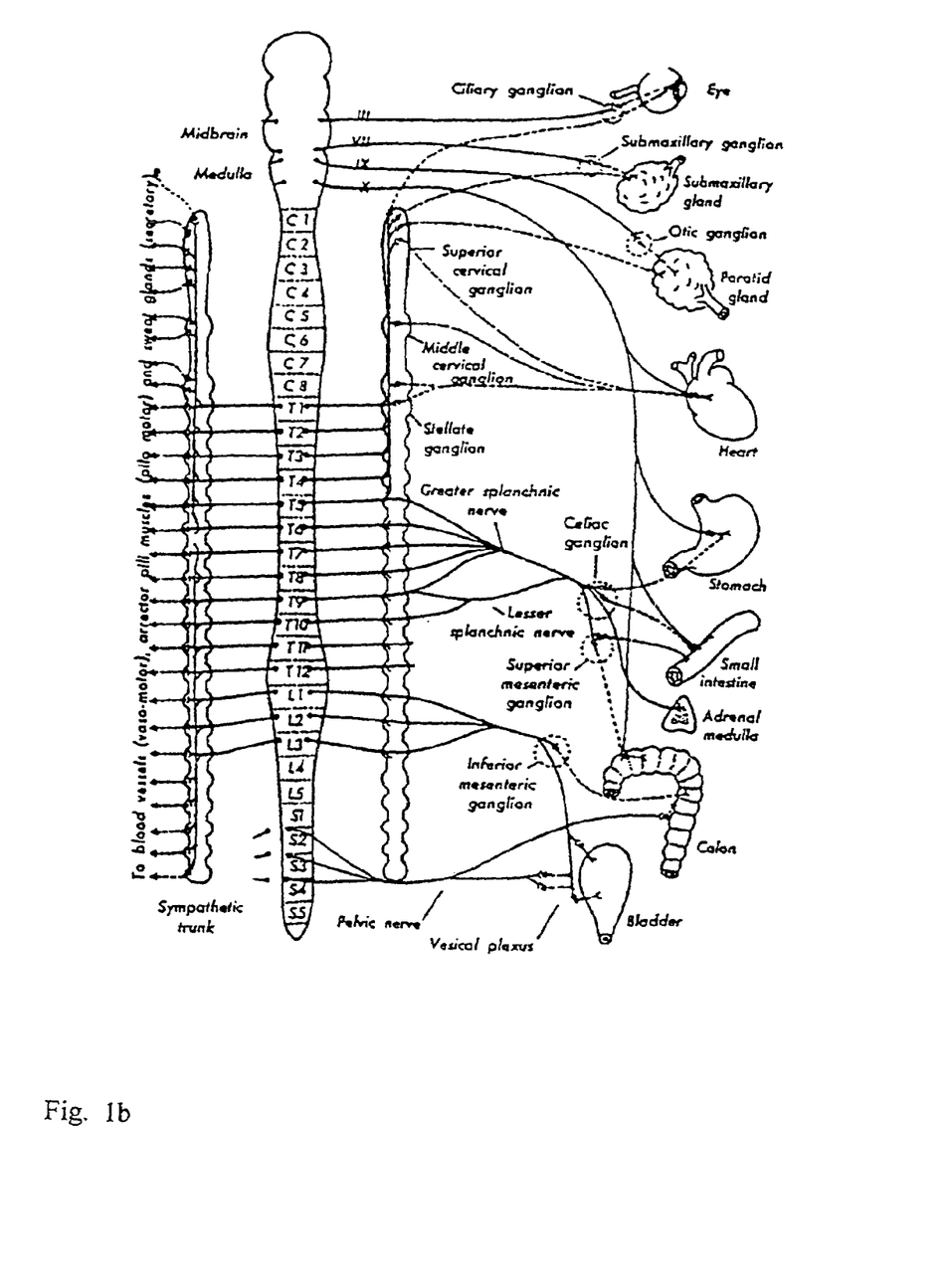
FIG. 1b shows the sympathetic nerve ganglia and their effectors.

FIGS. 1a and 1b show the relationship of back shu points and the sympathetic nerve ganglia. FIG. 1a shows the back shu points. FIG. 1b is the sympathetic nerve ganglia and their effectors. More specially, FIG. 1b shows that the effectors are eye, submaxillary gland, parotid gland, heat, stomach, small intestine, adrenal medulla, colon, and bladder. Actually every organ and every part of the body has a sympathetic nerve distribution. The effectors supplied by the sympathetic nervous system are the smooth muscles in all organs and some of the glands such as sweat, salivary, and digestive glands. In addition, sympathetic postganglionic fibers innervate adipose cells and liver cells.

The autonomic nervous system, including the adrenal medulla, through its integration relating to emotional behavior, prepared the body for somatic and visceral requirements. When the whole sympathetic system is activated, the combined sympathoadrenal responses resemble stress or anger. In Chinese acupuncture, meridian channels and acupoints are used in the treatment to make the unbalanced body balanced again. There are bladder channels on the back. In these channels there are several acupoints that are located on both sides of the spine from top to bottom of the back. These acupoints are closely related with organs. They were named shu points such as Lung shu, Heart shu, Jieyin (pericardia)shu, Du shu, Diaphragm shu, Liver Shu, Gallbladder shu, Spleen shu, Stomach shu, Triple burner shu, Kidney Shu, Qi sea shu, Large intestine shu, Guan yuan shu, Small intestine shu, and Bladder shu. The shu points are also called "back shu points" because of their sites. They are specific points on the back where the energy of the respective organ is infused. They are often used for diagnosis and treatment of disorders of the internal organs. The back shu points are in similar horizontal and vertical levels of the body to the sympathetic nerve ganglia. If one compares the names of shu points and the effectors of sympathetic nerve ganglia, one can find they are very similar.

The treatment of the invention is based on the belief that the back Shu points are the representatives on the skin locations of the sympathetic nerve ganglia. Since Shu points and sympathetic ganglia have this relationship, the back Shu points treatment can have the calming down effects for the sympathetic nervous system. In other words, when the sympathetic nerves are excited, their representative locations can be treated in order to calm down the hyperstimulated sympathetic nerves. Beside the back of the body, every part of the skin on our body has sympathetic nerve endings. They can be used for the treatment.

Figure 6:
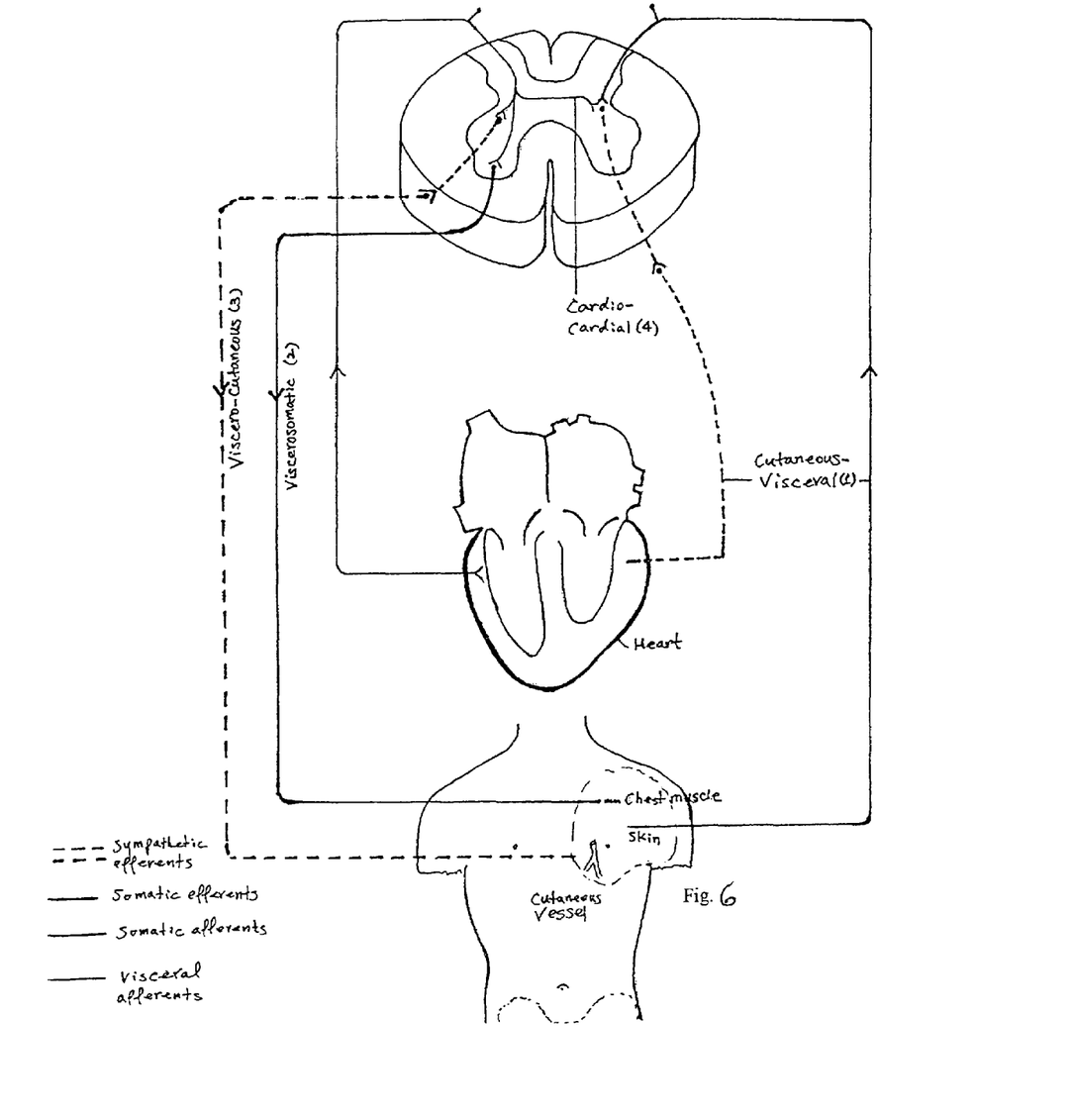
FIG. 6 shows the segmental spinal reflexes.

Segmental organization can characterize the afferent and autonomic innervation of certain organs. FIG. 6 path 4 shows the segmental spinal reflexes. Afferents from the heart and from the excretory organs make sympathetic contact, at a segmental level, with preganglionic sympathetic and parasympathetic neurons innervating the same organs such as cardio-cardial reflexes, intestino-intestinal reflexes, evacuation reflexes, etc. It is likely that similar specific spinal-segmental reflexes are also associated with other organs. The segmental organization of the autonomic innervation of organs can also be observed in the clinic. When viscera are in a pathological condition, the musculature over the site of the disorder is taut and the area of the skin innervated by afferents and efferents of the same spinal-cord segment that serves the affected organ is red. This phenomenon is explained by an inhibitory action of the afferents from the affected viscus on the sympathetic cutaneous vasoconstrictor efferents from the same segment that caused the red skin (FIG. 2, path 3) and an excitatory action on motoneurons that causes the protective tension of the chest musculature (FIG. 2, path 2). Conversely, pain or temperature stimulation in the skin causes reflex inhibition of the viscera innervated by the same spinal segment, by way of sympathetic neurons (FIG. 2, path 1). Visceral pain ascribed to the skin is called referred pain. In the clinic the referred pain means that the visceral pain is ascribed to the skin. It is likely that cutaneous nociceptive (pain) and non-nociceptive afferents and visceral efferents of a given spinal segment converge onto the same neurons of the spinothalamic tract. Thus, some of the information about the origin of the excitation from the internal organs is lost, and the cortex ascribes the excitation to the corresponding skin area as well. For example, the pain in the left chest, shoulder, and left arm may be the indication from angina pectoris resulting from inadequate perfusion of the coronary vessels. The right upper abdominal pain is related to gallbladder inflammation. Stomach ulcer can also be accompanied by left upper abdominal pain. Since the cutaneous region and the internal organ of a given segment share the same neurons of the spinothalamic tract, stimulating the skin calms down the overexcited internal organs.

The shu acupoints on the back share the same segmental character with the autonomic nervous system. The shu points are on the skin and their function is for treating related organs. For example, lung shu is for treating bronchitis, asthma, pneumonia, pulmonary tuberculosis, afternoon fever, and night sweat. Heart shu is for treatment of cardiac pain, palpitation panic, loss of memory, nocturnal emission, mania, and epilepsy. Liver shu is for the treatment of jaundice, pain in the hypochondriac region, and redness of eye. Gallbladder shu is for the treatment of jaundice, bitter taste of mouth, pain in the chest, hypochondriac region, pulmonary tuberculosis, and afternoon fever. Spleen shu is for treating epigastric pain, abdominal distension, jaundice, vomiting, diarrhea, dysentery, bloody stools, profuse menstruation, edema, anorexia, and backache. Stomach shu is for relieving pain in the chest and hypochondriac and epigastric regions, anorexia, abdominal distension, borborygmus, diarrhea, nausea, and vomiting. Kidney shu is for treating nocturnal emission, impotence, enuresis, irregular menstruation, leukorrhea, low back pain, weakness of knee, dizziness, tinnitus, deafness, asthma, and diarrhea. Large intestine shu is for treating low back pain, borborygmus, abdominal distension, diarrhea, constipation, muscular atrophy, pain numbness, motor impairment of the lower extremities, and sciatica. Small intestine shu is for treating lower abdominal pain, distension, dysentery, nocturnal emission, hematuria, enuresis, morbid leukorrhea, lower back pain, and sciatica. Bladder shu is for treating retention of urine, enuresis, frequent urination, diarrhea, constipation, stiffness and pain of lower back.

Since the function of these back shu acupoints also has a segmental characteristic just like the sympathetic ganglia, the back shu acupoints are the skin representatives of the sympathetic nerve ganglia. The stimulation on the skin region through the afferent into the spinal tract and the stimulation sent out through sympathetic nerve ganglia to the internal organs is to adjust its function.

The mechanisms of acupuncture are unknown so far. Experiments show that at the cuticle layer of the skin, meridian channels and acupoints have lower resistance to electricity, or higher electric conductivity, than the adjacent skin area. There is a high density of nerves and blood vessels in the epidermis and dermis layers of a meridian channel.

Using a magnetic hammer stimulating the cutaneous region of a meridian channel can get an effect similar to that of acupuncture. In other words, through magnet-electrical stimulation on the skin the sympathetic nervous system can be calmed down. This magnetic hammer tapping treatment can reduce the frequency, intensity, and duration of panic attacks.

EXAMPLES

Example 1

A man had panic attacks 2-3 times a week. The symptoms were increased heart rate, hyperventilation, stomach discomfort, and fear of being sick. Each panic attack lasted about 10 minutes and left the man tired. Magnetic hammer tapping was used on the man's back on both sides 1.5 inches off the spine from thoracic level 3 (T3) to lumbar 2(L2). The tapping width was about 1 inch at T3 to L1 level and about 3 inches at the L2 level. The tapping took about 5 minutes until the skin turned pink. After the first treatment, the man did not have any more panic attacks and felt more energetic. He has received this treatment twice a month for 2 months. His emotional status is stable.

Example 2

A 21-year-old young woman has panic attacks when she was in college and working. She had to quit college because of her anxiety. She still had to take an exam to complete a course. She didn't have any confidence because she was afraid that she would have a panic attack during the exam. She was treated 5 times. The treatment was on her back on both sides 1.5 inches off the spine from thoracic 3 (T3) to lumbar 2 (L2) level. The tapping width was about 1 inch at T3 to L1 level and about 3 inches at L2 level. The tapping made the skin pink. Each treatment took about 5 minutes. Several days after the last treatment she took the exam. She was very calm and passed it successfully. She said a relaxed emotional situation was impossible without these treatments.

Example 3

A woman had a panic attack and insomnia every evening. She was given the magnetic hammer and she treated herself on her lap every evening before going to bed. She used the magnet hammer to tap both legs until the skin turned pink. Each tapping area was about 1 foot long and about 1 inch wide. Since starting the treatment, she has experienced no panic attacks in the evening and her sleeping has improved. She was informed that if she feels stressful she should use the magnet hammer to do the lap tapping again until the symptoms disappear.

Example 4

A woman had several jobs and was going to school at the same time. She felt stressful all the time. After the treatment she felt calm and peaceful. She said she liked this treatment. The treatment was on the back on both sides 1.5 inches off the spine from thoracic 3 to lumbar 2 level. The tapping width was about 1 inch at T3 to L1 level and 3 inches at lumbar 2 level. Each treatment took 5 minutes until the skin turned pink. She had 4 treatments. So far she has been good for two months.

Example 5

A 21-year-old young man had been sexually abused when he was 6 years old. Since then he has felt stressful. He is a singer. Due to the stress he had difficulties with his singing training. He said: "Let me calm down!" He was treated on the back on both sides 1.5 inches off the spine from thoracic 3 to lumbar 2 level. The tapping width was about 1 inch at T3 to L1 level and 3 inches at lumbar 2 level. The treatment tool about 5 minutes. Immediately after the treatment, he said: "I feel better now." After three more treatments within 12 days, he quit the therapy because he could sing again.

Example 6

A graduate student had severe stress before the qualifying exam. He was very jittery and had a panic attack when he saw the exam paper. The graduate student treated himself by tapping on his lap. He used the magnet hammer to tap his lap on both legs until the skin turned pink. Each tapping area was about 1 foot long and 1 inch wide. After each treatment the tension in his back muscles was relieved. About 10 minutes later, he felt relaxed emotionally and could smile. Fifteen days later he had his qualifying exam with a calmed mental status and passed it successfully. It is believed that this student may need treatment only before exams.

Example 7

A fifty-year-old man had panic attack and agoraphobia. He couldn't go shopping and had difficulty driving a car. He received magnetic hammer tapping treatment. The treatment was on the back on both sides 1.5 inches off the spine from thoracic 3 to lumbar 2 level. The tapping width was about 1 inch at T3 to L1 level and 3 inches at lumbar 2 level. The treatment took about 5 minutes. He had this treatment once a week for two months. After the first 4 treatments, he could go shopping in the grocery store or hardware store but couldn't go to the big mall. After the eighth treatment he drove from Baltimore to Philadelphia without any trouble and he went to "Towson Town Center" alone without a panic attack.

Example 8

A 40 year-old man had panic attack approximately once a week for more than 10 years. At the start of magnetic hammer tapping therapy, his panic attack level was a 10 in frequency, intensity, and duration, on a scale of 0-10. The treatment area was on the back on both sides, 1.5 inches off the spine, from thoracic 3 to lumbar 2 level. The tapping width was about 1 inch at T3 to L1 level and 3 inches at lumbar 2 level. Each treatment took about 5 minutes. He received this treatment once a week for two months. Since then, the panic disorder has dropped to a level of 4 in frequency and 5 in intensity and in duration. He felt that he has become a much happier person and expected to continue the treatment.

Example 9

A 43-year-old male had experienced panic attacks while driving on the beltway. The attacks would occur 1 or 2 times every six months. Symptoms included rapid heart beat, shallow breathing and sweaty palms. The duration of the attack was about 15 minutes. A single magnetic hammer tapping treatment was performed. The treated area was on the back on both sides, 1.5 inches off the spine, from thoracic 3 to lumbar 2 level. The tapping width was about 1 inch at T3 to L1 level and 3 inches at lumbar 2 level. Since being treated, the frequency of the attacks has remained the same but the intensity has been reduced by about 50-60% and the duration has been reduced to about 1-2 minutes. He had only one treatment. He was surprised and pleased by the results.

We claim:

1. A method of treating anxiety disorders, diagnosable as a psychiatric illness, comprising tapping areas of the skin on the body with a hammer until the skin becomes pink, and wherein the head of the hammer that contacts the skin does not have a sharp protrusion that can penetrate the skin, and wherein the tapping area is in the back on both sides of the spine, about 1 to about 2 inches away from the spine between the thoracic vertebral 3 and the sacroiliac vertebral 4 level wherein the width of the tapping area is about 1 to about 1.5 inches on both sides of the spine and wherein tapping area is at about lumbar 2 vertebral level, the width of the tapping is about 3 to about 4 inches on both sides of the spine.

2. The method of claim 1 wherein the hammer has a magnetic head.

3. The method of claim 2 wherein the magnetic head has a magnetic strength of 100-14000 gauss.

4. The method of claim 3 wherein the magnetic head has a magnetic strength of 800-2000 gauss.

5. The method of claim 1 wherein the hammer is a rubber head hammer, a wooden head hammer, or a plastic head hammer.

6. The method of claim 1 wherein the tapping area is about 1.5 inches away from the spine.

7. The method of claim 1 wherein the step of tapping consists essentially of the area set forth in claim 1.

8. The method of claim 1 wherein the tapping is performed for about 5 to about 10 minutes.

9. The method of claim 1 wherein the tapping frequency is at least once a week.

10. The method of claim 1 wherein the anxiety disorder being treated is selected from the group consisting of panic attacks, or posttraumatic stress disorder.

11. A method of treating anxiety disorders, diagnosable as a psychiatric illness, comprising tapping areas of the skin on the body with a hammer until the skin becomes pink, wherein the head of the hammer that contacts the skin does not have a sharp protrusion that can penetrate the skin, and wherein the tapping area is on the outer side of the upper arm or the outer side of the forearms; on the front, side, or back or the side of the lower legs; on the abdomen, about 0.5 inch to about 1 inch away from the navel, about 2 to about 3 inches in all directions from the navel; or on the buttocks.

12. The method of claim 11 wherein the tapping area is on the outer side of the upper arms or the outer side of the forearms.

13. The method of claim 11 wherein the tapping area is on the front, side, or back of the upper legs, or the back or side of the lower legs.

14. The method of claim 11 wherein the tapping area is on the abdomen, about 0.5 inch to about 1 inch away from the navel, about 2 to about 3 inches in all directions from the navel.

15. The method of claim 11 wherein the tapping area is on the buttocks.

16. The method of claim 11 wherein the step of tapping consists essentially of the area set forth in claim 11.

17. The method of claim 11 wherein the hammer has a magnetic head.

18. The method of claim 11 wherein the anxiety disorder being treated is selected from the group consisting of panic attacks, or posttraumatic stress disorder.

\* \* \* \* \*